(12) United States Patent
Domankevitz (10) Patent No.: US 9,919,167 B2
(45) Date of Patent: Mar. 20, 2018

(54) MULTIWAVELENGTH ULTRASONIC TISSUE TREATMENT APPARATUS

(71) Applicant: LUMENIS LTD., Yokneam Ilit (IL)

(72) Inventor: Yacov Domankevitz, Zichron Yaacov (IL)

(73) Assignee: LUMENIS LTD., Yokneam Ilit (IL)

( * ) Notice: Subject to any disclaimer, the term of this patent is extended or adjusted under 35 U.S.C. 154(b) by 203 days.

(21) Appl. No.: 14/812,588

(22) Filed: Jul. 29, 2015

(65) Prior Publication Data

US 2016/0030772 A1 Feb. 4, 2016

Related U.S. Application Data

(60) Provisional application No. 62/032,145, filed on Aug. 1, 2014.

(51) Int. Cl.
*A61N 7/00* (2006.01)

(52) U.S. Cl.
CPC ........ *A61N 7/00* (2013.01); *A61N 2007/0008* (2013.01); *A61N 2007/0034* (2013.01); *A61N 2007/0073* (2013.01); *A61N 2007/0078* (2013.01)

(58) Field of Classification Search
CPC .................................... A61N 7/02; A61N 7/00
See application file for complete search history.

(56) References Cited

U.S. PATENT DOCUMENTS 6,500,141 B1 * 12/2002 Irion ........................ A61N 7/00
601/2
2014/0276055 A1 * 9/2014 Barthe ...................... A61N 7/02
600/439

* cited by examiner

*Primary Examiner* — Hien Nguyen
(74) *Attorney, Agent, or Firm* — ISUS Intellectual Property PLL; A. Jason Mirabito (57) ABSTRACT

An apparatus for the treatment of skin tissue includes at least one ultrasound transducer for placement on the skin tissue surface; at least two drivers for driving the at least one transducer; a controller which is configured to control the at least two drivers; the controller is configured to drive the at least two drivers at different frequencies to affect different depths in the skin tissue.

12 Claims, 7 Drawing Sheets

MULTIWAVELENGTH ULTRASONIC TISSUE TREATMENT APPARATUS

RELATED APPLICATIONS

This application claims priority to U.S. Provisional Patent Application No. 62/032,145, filed Aug. 1, 2014, the disclosure of which is hereby incorporated by reference in its entirety.

FIELD OF THE INVENTION

The present invention relates to an apparatus and method for treating a human body with multiple wavelengths of therapeutic ultrasound probe.

BACKGROUND OF THE INVENTION

Ultrasound is widely used for both diagnostic and therapeutic procedures. Therapeutic ultrasound includes a variety of procedures concerned with diseases or aesthetic treatments. Body shaping and contouring occupies a significant role in aesthetic ultrasound treatments, in which fat cell destruction is accomplished by applying low frequency ultrasound to a desired area of the skin. In this type of fat treatment, energy is primarily delivered to the subcutaneous layers of the skin where fat cells are heated until lipolysis occurs.

To achieve this desired effect, an ultrasound probe is positioned on the patient's skin and ultrasonic (hereinafter "US") energy heats the deeper skin layers. This known treatment may require a long continuous application of US energy and may have undesirable side effects such as raising the temperature of the shallower skin layers closer to the skin surface.

Alternatively, focused ultrasound probe may be employed to focus higher densities of energy at a required depth to achieve a similar lipolysis effect. However, such a type of US energy beam is focused on a smaller treatment spot and thus usually requires a prolonged treatment to cover a desired body treatment area.

Skin tightening is another common aesthetic procedure which may be done using US energy. Skin tightening is achieved by shrinking and or producing new collagen in the dermis layer of the skin.

Thus, there is a perceived need to provide a non-focused US energy delivery apparatus which has the capability to destroy fat cells, while keeping the skin surface cool as well as providing shallow skin tightening in one single apparatus.

SUMMARY OF THE PRESENT INVENTION

In one aspect, an apparatus for the treatment of skin tissue includes at least one ultrasound transducer for placement on the skin tissue surface; at least two drivers for driving the at least one transducer; a controller is configured to control the at least two drivers and the controller is configured to drive the at least two drivers at different frequencies to affect different depths in the skin tissue.

In another aspect, the at least one transducer is two or more transducers, each of the two or more transducers being operable at different frequencies.

In yet another aspect, the at least one transducer is a composite transducer, and the composite transducer being operable at more than one frequency; a first one of the at least two drivers operates to affect deep skin tissue and another of the at least two drivers operates to affect more shallow skin tissue.

In another aspect, the first one of the at least two drivers causes fat heating and wherein the another of the at least two drivers causes skin-tightening. In addition, the controller may be configured to drive the at least two drivers one of sequentially or simultaneously.

In yet a further aspect, an even-sided polygonal-shaped hollow housing is provided and one or more pairs of transducers are mounted within the housing and arranged such that complementary pairs of transducers face each other; more than one pair of transducers may be provided, and the pairs of transducers may be activated by the controller to operate at one of the same or different frequencies.

In a further aspect, the more than one pairs of transducers may be activated by the controller one of sequentially or simultaneously and the activation of the more than one pairs of transducers causes one or more of skin tightening and fat heating.

In another aspect, a cooling plate is mounted on the at least one ultrasonic transducer such that the cooling plate, when positioned, is between a bottom surface of the at least one transducer and the skin tissue surface.

In yet a further aspect, the controller is programmed to activate the at least two drivers and the cooling plate in a sequence of: first to activate the cooling plate to cool the skin tissue to a predetermined temperature, followed by the activation of the at least two drivers at different frequencies to affect skin tissue heating; the controller may be programmed to repeat the activation X number of times.

In an aspect, the temperature of fat in the skin tissue reaches 42 to 50 degrees C.; the apparatus further includes a housing having a top wall portion and a side wall portion, the top wall portion and the side wall portion forming a cavity, wherein the at least one transducer is mounted in the cavity in top wall portion and slidable away from the top wall portion to compensate for differences in skin tissue structure.

In another aspect, the apparatus may include a device for causing suction within the cavity, the suction, when activated by the controller, causing skin tissue to contact the at least one transducer. The apparatus may include two or more ultrasound transducers for placement on the skin tissue surface, the two or more transducers being angled with respect to the tissue surface towards one another such that, when activated by the controller, the ultrasound energy delivered to the skin tissue by the two or more transducers is superimposed.

DETAILED DESCRIPTION OF THE PRESENT INVENTION

Dual Wavelength Ultrasonic Probe

Ideally, a ceramic transducer should be operated at its resonant frequency in order to achieve optimal performance. One object of the present invention is to drive a ceramic transducer with two different frequencies. The first frequency can be on resonance to achieve optimal performance, while the second frequency can be off resonance to achieve less than optimal performance. The result, however, is not optimal in terms of energy conversion and efficiency. A dual frequency ultrasonic probe can be realized in a simple single transducer flat geometry or a multiple faced probe.

Thus, the present invention is directed to an ultrasound probe that operates in at least two different wavelengths either simultaneously or sequentially for achieving different effects on the skin, including deep fat heating and shallow skin tightening, all in one apparatus. It is desirable to combine these treatments because once the fat tissue volume is reduced by the action of deep fat heating, the overlying skin surface may become wrinkled or saggy. The shallow skin-tightening treatments may help to reduce such wrinkling or sagging skin.

Figure 1:
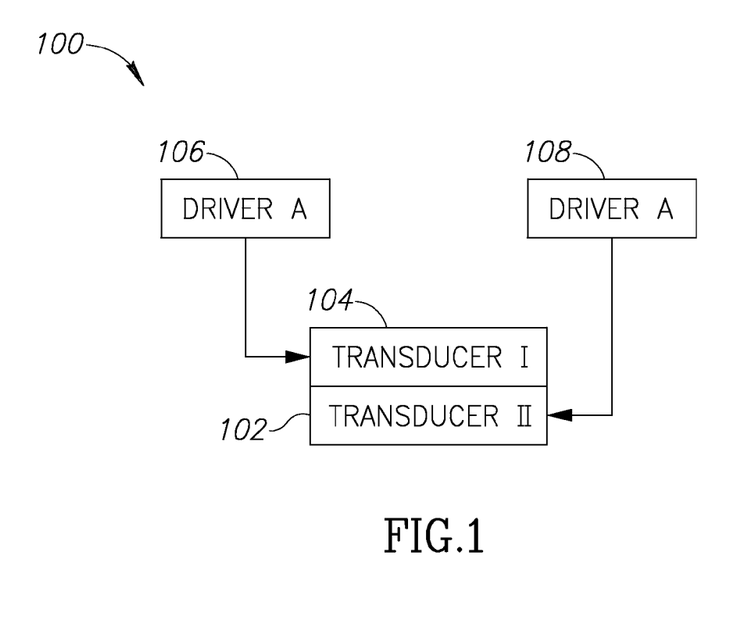
FIG. 1 illustrates a first embodiment of a dual wavelength US transducer arrangement.
Figure 2:
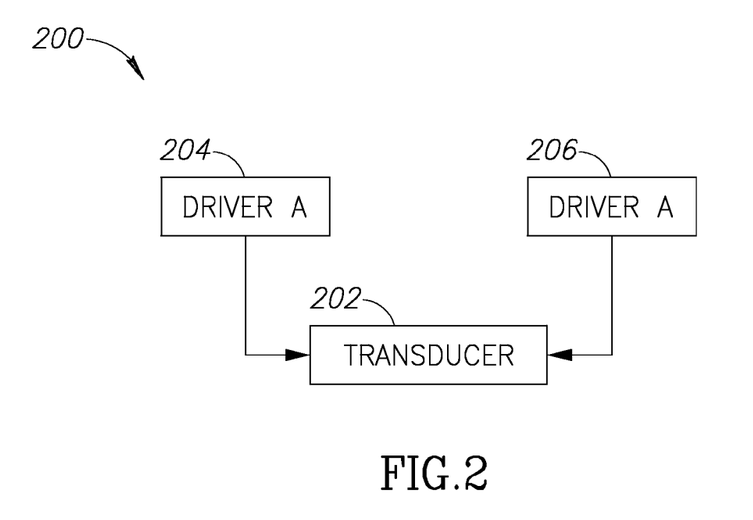
FIG. 2 illustrates a second embodiment of a dual wavelength US transducer arrangement.

Ultrasound transducers are generally well-known devices that vary in types and the width of the frequency range within which each US transducer operates. One type, piezo-electric transducers, are relatively cheap but operate in a defined resonance frequency. Composite transducers are also available but are more expensive but allow a wider frequency spectrum. In order to operate in at least two different wavelengths, two different embodiments are illustrated in FIGS. 1 and 2. A first embodiment includes two piezoelectric transducers, and each transducer may be chosen to operate at a different resonance frequency. A second embodiment includes a single composite transducer which operates in a wider frequency spectrum.

FIG. 1 illustrates the first embodiment of a dual wavelength probe 100. The dual wavelength probe 100 is shown as comprising two transducers, 102 and 104. Transducer 102 and transducer 104 may be arranged in any configuration in which each transducer treats the same area of skin but to different depths.

Transducer 102 and transducer 104 are respectively controlled by driver B (108) and driver A (106). The transducers 102 and 104 can be made to be operated either simultaneously or sequentially. Each one of the transducers 102 and 104 operates in a defined range of frequencies to affect different depths in the skin. For example, transducer 102 may operate in a low frequency range (about 200 kHz to about 2 MHz) to affect fat tissue by heating the fat tissue and raise the temperature in this area, while transducer 104 may operate in high frequency range (about 2 MHz to about 10 MHz) to affect the dermis layer and cause skin tightening. While two transducers are shown in FIG. 1, it is to be understood that this is for the purposes of illustration only and any number of transducers and their drivers may be utilized. A programmable controller (not shown but conventional) may be included to control the operation of the at least one transducer, the two or more drivers as well as a cooling device to be discussed below in connection with FIG. 4. The controller may be programmed and configured to cause activation of, for example, the drivers, the transducers and the cooling device in a sequence selectable by an operator to cause the desired effects on the skin tissue.

FIG. 2 illustrates a second embodiment of a dual wavelength probe 200. The dual wavelength probe 200 comprises a single transducer 202, in this case a composite transducer, but is driven and controlled by two drivers 204 and 206. Each driver can control transducer 202 to operate in a different frequency range for treating two different layers at different depths of the skin, as discussed in relation to FIG. 1 above. As with the first embodiment, while two drivers are illustrated, any number of drivers and transducers may be utilized.

Figure 3A:
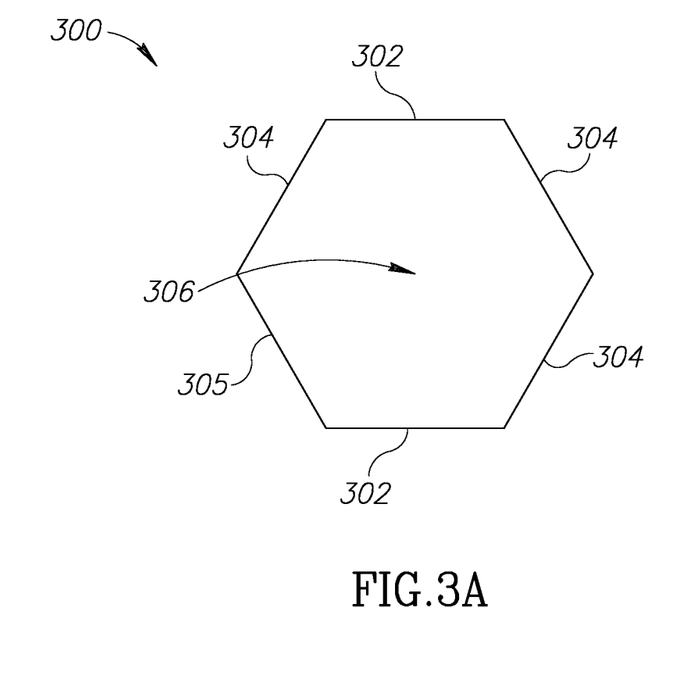
FIGS. 3A and 3B illustrate an embodiment of a US transducer arrangement mounted in a polygonal-shaped device.

FIG. 3A illustrates a top view of an embodiment of a multi wavelength probe 300. The multi wavelength probe 300 is shown in a structure having a hexagon shape, but is not limited to that shape as any polygonal shape may be utilized. Each opposite side may comprise a transducer that operates in the same frequency range as its opposite transducer. Transducer pairs 302 may operate at a different frequency range than transducer pairs 304. A third transducer pair 305 may operate at either the same frequency range as 302 or 304 or an altogether different frequency range as desired. Increasing the number of sides of the polygonal structure will increase the number of pairings of transducers possible and vice versa.

Figure 3B:
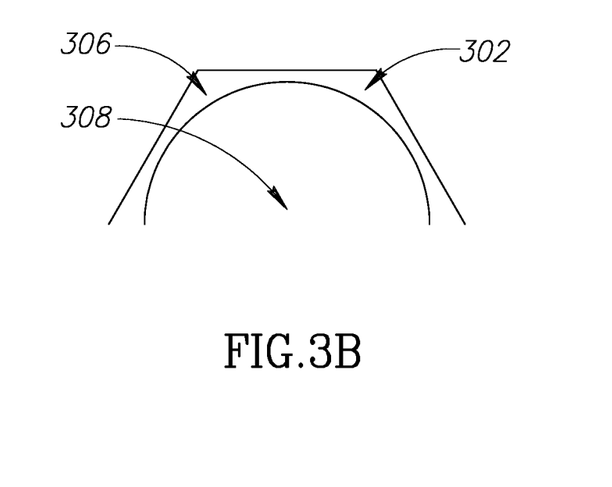

The multi wavelength probe 300 may also include a chamber 306 as shown in the side view of FIG. 3B. FIG. 3B illustrates the result of suctioning a portion of skin 308 into the interior of the probe by creating a vacuum in the chamber 306 in a known manner. When skin 308 is suctioned into chamber 306, each of the two opposing transducers may be made to operate in a defined frequency to apply energy to the desired area. One option is to operate transducers 302 of a low frequency to reach deep skin layers to affect fat tissue while transducers 304 may operate at a high frequency to reach shallow skin layers for skin tightening purposes, either simultaneously or sequentially.

The treatment of fat cells requires raising the temperature of the fat tissue layer. This procedure may sometimes be painful for the patient as the temperature of the shallower skin layers may also be raised. Cooling the outer skin layer's temperature while heating the deeper layers yields the same desired effect for the fat layer but allows a painless, more comfortable treatment.

Heating and Cooling with an Ultrasonic Transducer

Figure 4:
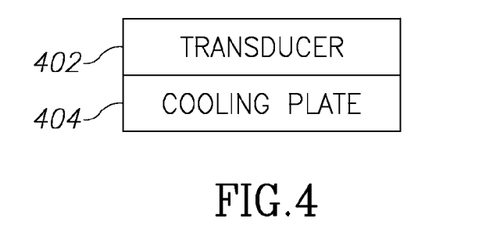
FIG. 4 illustrates an US transducer with a cooling plate that may be used in any of the embodiments of FIG. 1, 2 or 3A to 3B.

FIG. 4 illustrates one embodiment of a device for cooling the patient's outer skin layer while raising the temperature of the deeper fat layers. The device may under the control of and activatable by the controller discussed above. Since the dermis has an absorption 2 to 4 times that of fat, it is easier for the dermis to be heated than fat, and thus cooling of the is very desirable. As shown in FIG. 4, transducer 402 is coupled to a cooling plate 404. The cooling plate 404 can be made of any material that has a high thermal conductivity, including a metal. For example, Aluminum is a good conductor for imparting cooling energy to the skin but not so good as an acoustic coupler. This may be compensated for by provision of an acoustic resonator, as will be explained below in connection with the embodiment of FIG. 12.

This higher frequency, shallower penetration depth may occur with only a low temperature raising of about 5 to 15 degrees C. for skin tightening. To achieve the combination of the two desired effects of skin tightening and fat cells lipolysis in one treatment, the fat cells layer temperature should be raised to an effective level while keeping the shallower skin layer in controlled temperature range.

Figure 5:
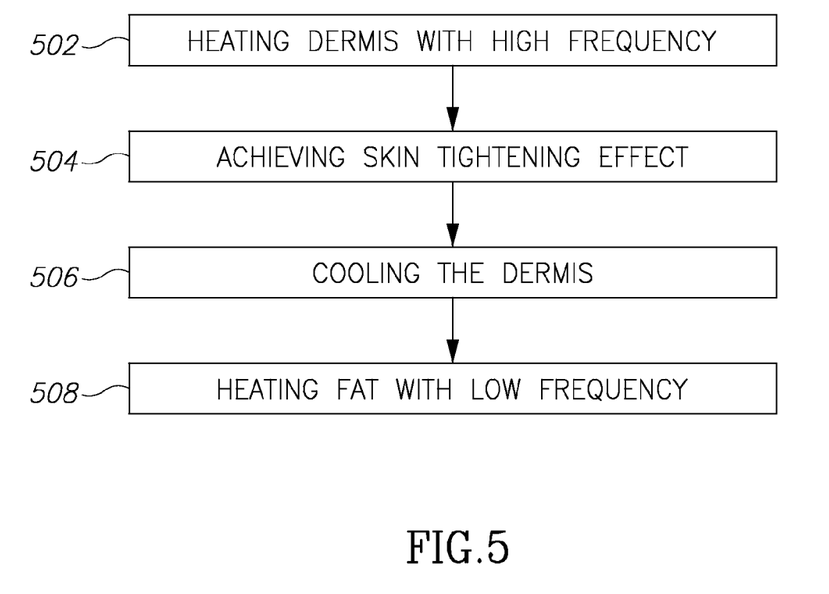
FIG. 5 illustrates a flow diagram of a sequence of fat heating and skin tightening using a dual wavelength transducer arrangement of the present invention.

FIG. 5 is a flow chart illustrating one sequence of treating two different skin layers while maintaining a convenient and comfortable treatment for the patient. The treatment may begin in step 502 with heating the dermis with high frequency energy. After achieving the desired skin tightening effect in step 504, in step 506 a cooling system cools the dermis while the effect of such cooling on the deeper layers is negligible. The deeper skin layers containing fat are then treated with lower frequency ultrasound in step 508. The ultrasound energy may increase the temperature of the deep skin layers to achieve the desired lipolysis effect while keeping the temperature of the shallower skin layers below a defined threshold.

Figure 6:
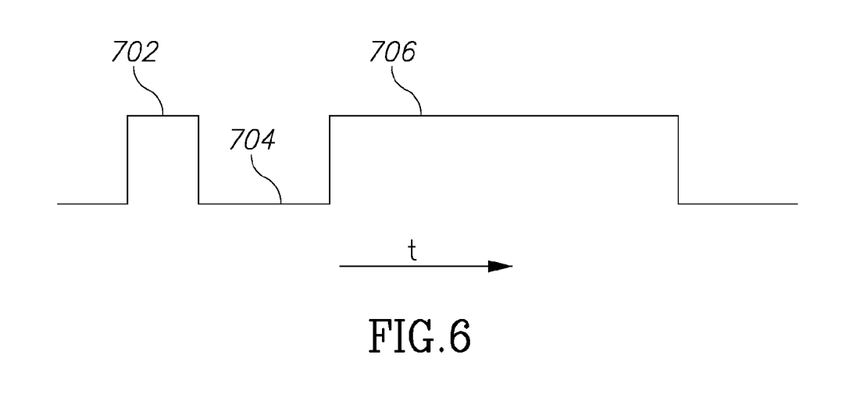
FIG. 6 is a graphical representation of temperature levels in both shallow and deeper skin layers when using the sequence of fat heating and skin tightening of FIG. 5.

FIG. 6 illustrates one configuration of sequences of ultrasound pulses applied for treating two different skin layers in accordance with the sequence of steps illustrated in FIG. 5. FIG. 6 illustrates that treatment may begin with the application of a high frequency ultrasound pulse 702 from a high frequency range transducer which aims to treat the dermis layer. The pulse is then halted in order to cool the dermis layer as shown at reference numeral 704. After that, a low frequency ultrasound pulse from a lower frequency range transducer is applied to treat fat cells layer for a longer time period, as illustrated by reference numeral 706.

Figure 7:
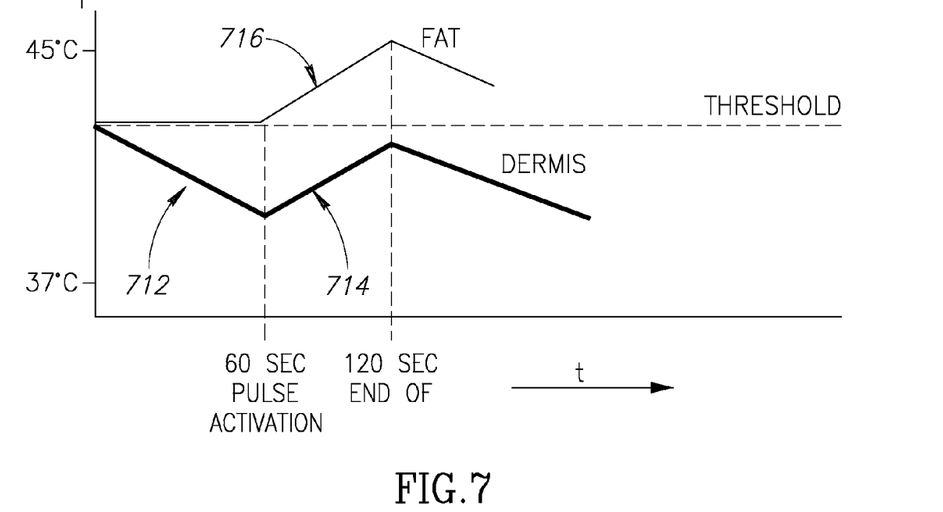
FIG. 7 is another graphical representation of the application of US pulses to the skin to target both deeper and shallower skin layers.

FIG. 7 illustrates the relative temperature levels within the fat layer and the dermis layer in the sequence of operations of FIG. 6. The aim is to keep the dermis cooler than the fat layer. This may be achieved by applying a sequence of pulses as illustrated in FIG. 7. As shown in FIG. 7, the dermis is cooled (at 712) below a set threshold temperature of, by way of example only, 37 degrees C. Then, both high and low frequency pulses are applied (shown here simultaneously by way of example) at 714 and 716 to the dermis and fat layers respectively. For the purposes of illustration, the pulses shown in FIG. 7 are shown as being of 60 seconds and 120 seconds of duration, but of course this may be changed or modified to suit the particular treatment parameters desired or planned. This causes both layers to increase in temperature, but the dermis layer is maintained below the set damage threshold temperature line shown in FIG. 7. The fat layer is seen to increase in temperature to around about 42-50 degrees C. for a long enough period to cause lipolysis. The sawtooth pattern of pulse shown in FIG. 7 may be repeated any number of times to achieve the results desired.

Individual patients' skin layers depth and thickness may vary and thus it may be necessary to adjust the application of the ultrasound energy to achieve the desired effect. The ultrasound probes themselves operate in a defined frequency range without considerations of variations in skin depths and thicknesses.

Adjustable Ultrasound Transducer

Figure 8:
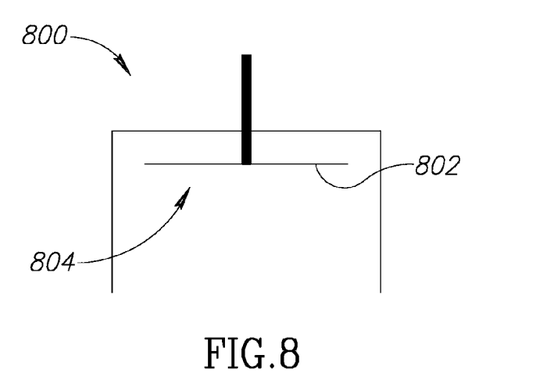
FIG. 8 illustrates another embodiment of a US transducer which is adjustable in a direction orthogonal to the patient's skin surface.

FIG. 8 illustrates one embodiment for an ultrasound probe 800 that compensates for the variation in the skin layers depths and thicknesses among patients. The ultrasound transducer 802 is positioned inside a cavity 804 and is slidable away from the top inside wall of the cavity. The skin can be suctioned by any means such as vacuum device under the control of the controller to move to inside the cavity 804 which may be similar to the structure of FIGS. 3A and 3B. The suction process brings the deep skin layers closer to the transducer 802. The amount of the skin suctioned can be controlled and determined according to other patient parameters such as BMI or imaging of skin layers.

Homogeneous Energy Distribution

Figure 9A:
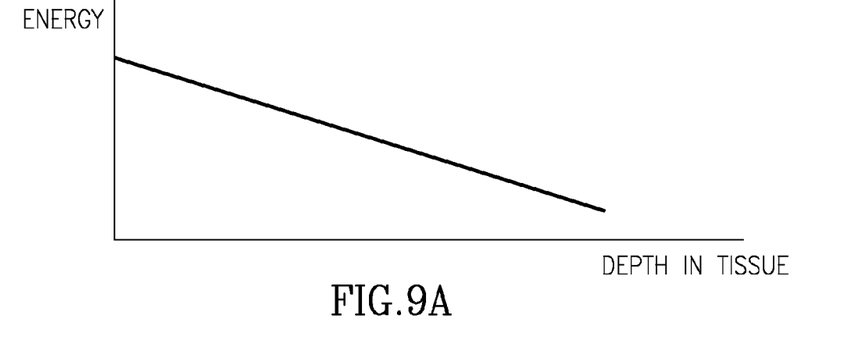
FIG. 9A to 9C illustrate another embodiment of a US transducer arrangement.
Figure 9B:
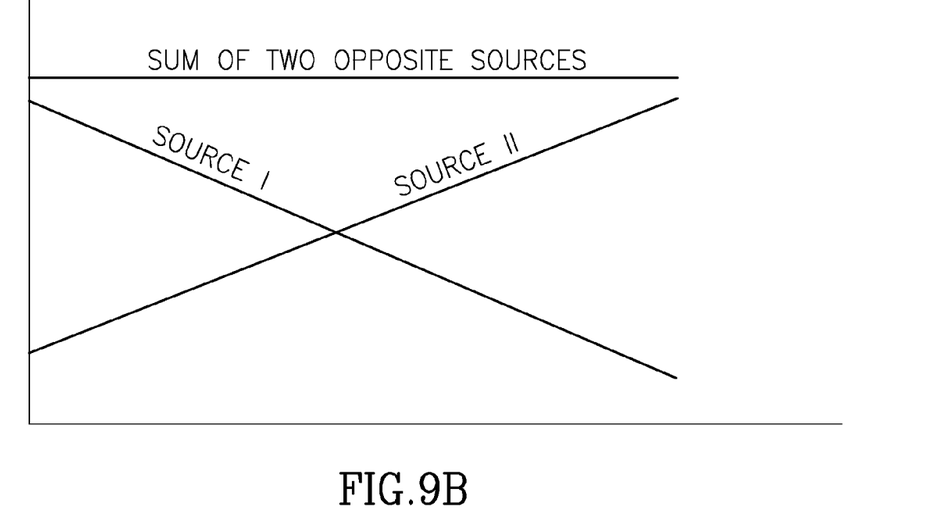

Energy that is applied to tissue is attenuated. Any energy source, whether applied from above or from the side of a folded tissue will attenuate. Energy distribution in the tissue will not be homogenous. The higher the frequency of the energy source, the stronger the attenuation by the tissue. FIG. 9A illustrates attenuation with a single source as a function of energy level and depth of penetration of the tissue. In order to provide a more or less homogeneous energy distribution, two opposite transducers, as illustrated in FIG. 9B may be deployed to achieve a more or less homogeneous distribution of energy within the tissue. The sum of the opposite sources are seen to result in a higher level, more uniform energy level as applied to the tissue.

Figure 9C:
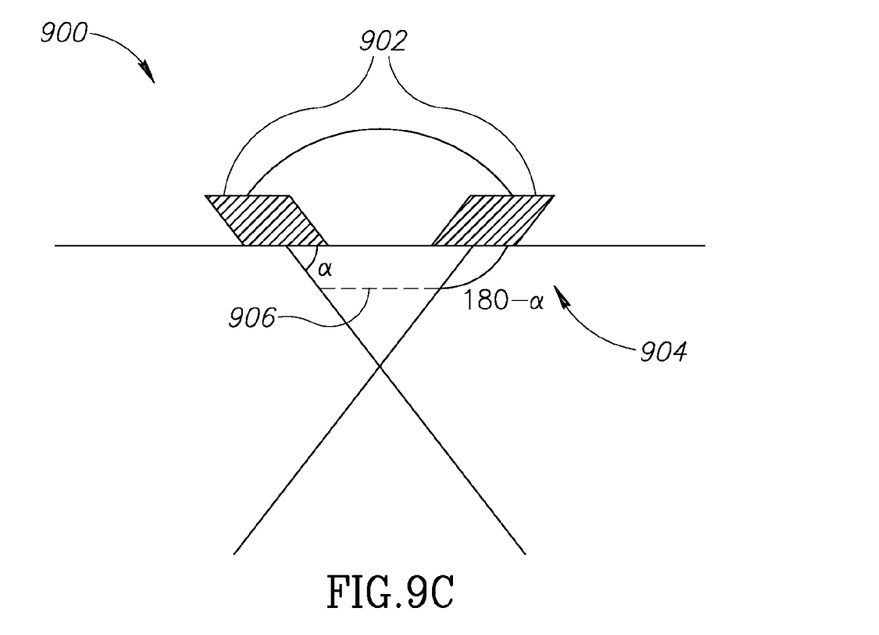

FIG. 9 illustrates an embodiment for an ultrasound device 900 for delivering homogenous energy to a large tissue area. Two identical transducers 902 are positioned to deliver ultrasound energy to a skin portion 904. The transducers 902 simultaneously apply the energy to the skin portion 904 while one of them delivers the energy at an angle α relative to skin surface and the other one at an angle 180—α relative to the skin. This arrangement causes the superposition of the two ultrasound energy distributions and results in a homogenous effect along skin layer 906, as seen in FIG. 9C. High frequencies of a few MHz, based on the superposition homogenation using two opposite transducers, may provide homogeneous energy distribution of about 3 cm in length while at lower frequencies of a few kHz, the attenuation is lower and therefore a bigger distance between opposite transducers about 6 cm will still yield a homogeneous distribution of energy within the tissue. It should be mentioned that homogeneous energy distribution within the tissue is relatively hard to achieve by treating the tissue from the top only. This homogenation process is achieved by creating a fold in the tissue using vacuum, and by applying US energy to opposite transducers which work simultaneously.

Combination of Light and Ultrasound Treatment

Laser energy is often used for treatment of the dermis layer. Fractional laser treatment has recently shown effective results for skin rejuvenation and skin tightening.

Figure 10:
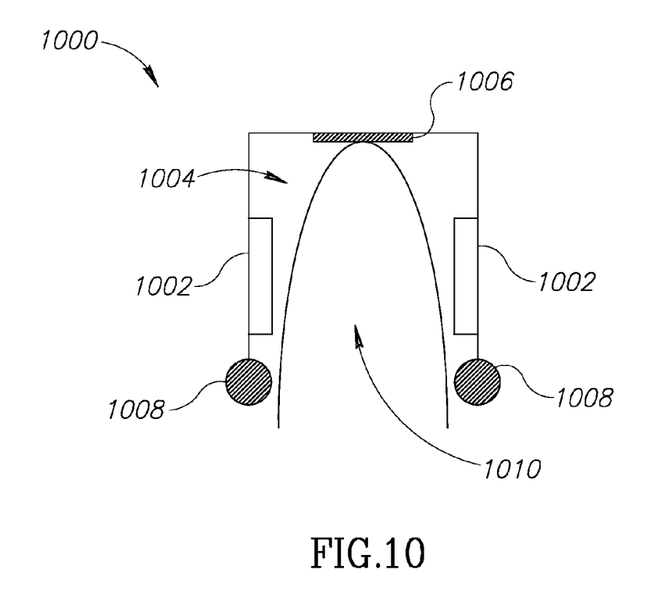
FIG. 10 illustrates another embodiment of a US transducer arrangement with a light-based treatment device, rollers and cooling apparatus.

FIG. 10 illustrates an embodiment of an ultrasound probe 1000 combined with fractional laser treatment. Two transducers 1002 are shown in this illustrative embodiment as being positioned inside cavity 1004. It is to be understood that while two transducers are illustrated, any suitable number of transducers may be utilized. In addition, a light source 1006 is positioned in the top portion of the cavity 1004 to apply either fractional or non-fractional energy to the shallower skin layers. A portion of the skin 1010 is suctioned into the cavity 1004. The two ultrasound transducers 1002 apply energy to homogenously treat the desired skin layers. In addition, the device may be provided with two rolling elements 1008 which are positioned on the bottom of the cavity and allow continuous movement of the probe 1000 along the skin. The rolling elements 1008 may also contain cooling devices to cool the portion of the skin that was treated and the portion of the skin that will be treated next. This movement also allows a homogenous treatment of the whole treated area as the speed of the rolling elements 1008 can be determined to compensate for the attenuation of the ultrasound energy. Transducers located on the top and the sides of the device may treat the tissue with high-frequency ultrasound energy to achieve a shallow skin tightening effect or each one of them may produce low-frequency ultrasound energy to target fat and together create a homogeneous energy distribution within the target tissue bulk. In an alternative embodiment, the ultrasound transducers may be cooled to also cool adjacent tissue.

Figure 11:
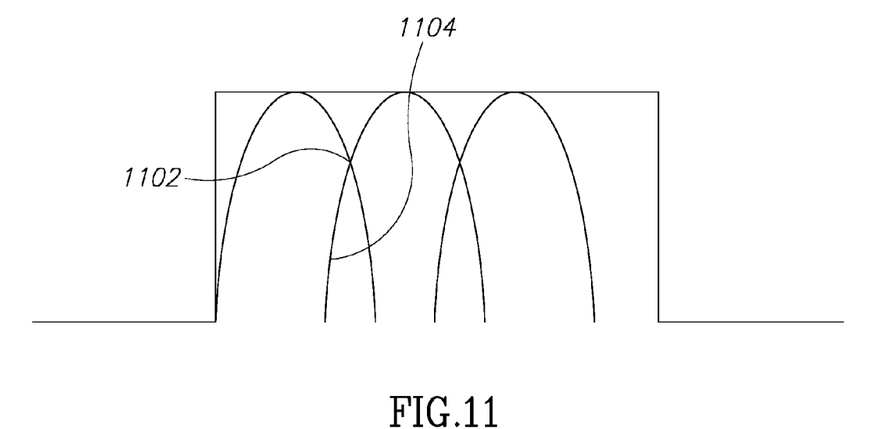
FIG. 11 illustrates US energy distribution with the US transducer arrangement of FIG. 10.

As shown in FIG. 11, by providing movable or rotatable transducer(s) within a US energy device, the energy of the side-lobe 1102 is summed with the energy of the side-lobe 1104 and tends to maintain a uniform energy level as applied to the skin.

Multiple Reflection Cascading Effects

As mentioned and discussed above with respect to the use of a metal plate to cool the skin surface, one problem is that of back reflections. Diagnostic ultrasound probes used for imaging are very sensitive to artifacts caused by such back reflections. Since acoustic index matching is not perfect, not all of the ultrasound energy penetrates the tissue. A portion of the energy is back reflected toward the transducer. However, some of the back reflected energy may be made to be reflected again towards the tissue. A portion of this energy then may also penetrate the tissue with a time delay relative to the main beam and cause artifacts. Therefore, a backing plate with high absorption properties may be introduced beyond the transducer so that any ultrasound energy reflected back from the tissue will be re-reflected through the transducer toward the tissue again. For treatment probes which operate under a HIFU-type regime, back reflections should also be avoided since these delayed reflected beams are not in sync anymore with the focal point of the main beams.

Energy transmitted by the transducer hits coupling layer with the tissue. Only a portion of the energy penetrates the tissue and another portion is reflected back. As mentioned above, one may use a metal coupling element which is not perfect in terms of ultrasound index matching. The metal coupling element, such as aluminum, allows for better cooling of the tissue. Such a non-perfect coupling element may cause about 50% of the original energy to penetrate the tissue. The other 50% will be reflected back.

Figure 12:
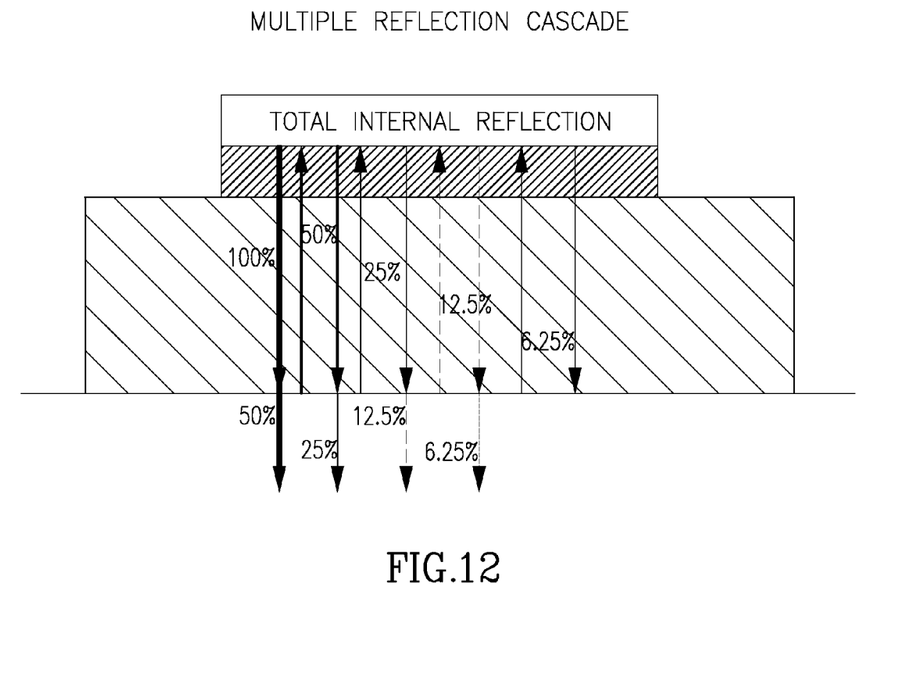
FIG. 12 illustrates a multiple reflection US transducer resonator arrangement.

In the present invention, the tissue is treated for relatively long time, so the duration of time for the application of the energy is not so critical. To achieve non-specific heat and since the aim is to heat the bulk of the tissue, the majority of the energy produced by the transducer may be drained by having a strong reflector such as air on the back of the transducer to enhance the back reflection effect described above and bring more and more energy into the tissue by the cascade of reflections so that about 99% of the energy produced by the transducer will eventually find its way into the tissue. This cascade of reflections is shown in FIG. 12, in which 50% of the arriving energy penetrates the tissue while about 50% of arriving energy will be reflected. There will be a lower quantum of energy at each step, that is, lower by 50%, as shown in FIG. 12.

What is claimed is:

1. An apparatus for a treatment of skin tissue comprising:
at least one ultrasound transducer for placement on the skin tissue surface;
at least two drivers for driving the at least one transducer;
a programmable controller configured to control an activation and operation of the at least two drivers;
wherein the programmable controller is configured to drive the at least two drivers at different frequencies to deliver ultrasound energy and to affect different depths in the skin tissue;
wherein the at least one transducer is two or more transducers, each of the two or more transducers being operable at different frequencies, one frequency being a high frequency range of 2 MHz to 10 MHz to treat a dermis layer to cause skin tightening, another frequency being a low frequency range of 200 KHz to 2 MHz to treat fat cells;
the apparatus further comprising a cooling plate mounted on the transducers such that the cooling plate, when positioned, is positioned between a bottom surface of the transducers and the skin tissue surface;
wherein the programmable controller is programmed to activate and operates the at least two drivers and the cooling plate in a sequence of first causing the activation of a high frequency pulse for a period of time from the transducer operable at a high frequency range to treat the dermis layer and cause skin tightening, next halting the operation of the high frequency pulse, next activating the cooling plate to cool the dermis layer for a period of time, and next causing the activation of a low frequency pulse from the transducer, operable at a low frequency range to treat fat cells; and
wherein the period of time of activation of the high frequency pulse is X, the period of time of activation of cooling by the cooling plate is Y, and the period of time of activation of the low frequency pulse is Z, and wherein Z>Y and Z>X.

2. The apparatus of claim 1 wherein each of the two or more transducers is a composite transducer, the composite transducer being operable at more than one frequency.

3. The apparatus of claim 1, wherein a first one of the at least two drivers operates to affect deep skin tissue and another of the at least two drivers operates to affect more shallow skin tissue.

4. The apparatus of claim 1 wherein the programmable controller is configured to drive the at least two drivers one of sequentially or simultaneously.

5. The apparatus of claim 1, further comprising an even-sided polygonal-shaped hollow housing and wherein at least two transducers form a pair of transducers and are mounted within the housing and arranged to face each other.

6. The apparatus of claim 5, comprising more than one pair of transducers, and wherein the pairs of transducers are activated by the programmable controller to operate at one of the same or different frequencies.

7. The apparatus of claim 6, wherein the more than one pairs of transducers are activated by the programmable controller one of sequentially or simultaneously.

8. The apparatus of claim 7 wherein the activation of the more than one pairs of transducers causes one or more of skin tightening and fat heating.

9. The apparatus of claim 1, wherein the programmable controller is programmed to repeat the activation X number of times.

10. The apparatus of claim 1, wherein the temperature of fat in the skin tissue reaches 42 to 50 degrees C.

11. The apparatus of claim 1, further comprising a housing having a top wall portion and a side wall portion, the top wall portion and the side wall portion forming a cavity, wherein at least one transducer is mounted in the cavity in top wall portion and slidable away from and toward the top wall portion to compensate for differences in skin tissue structure.

12. The apparatus of claim 11, further comprising a device for causing suction within the cavity, the suction, when activated by the programmable controller, causing the skin tissue surface to contact the at least one transducer.

* * * * *